United States Patent

Bencini et al.

Patent Number: 5,172,700
Date of Patent: Dec. 22, 1992

[54] DISPOSABLE BIOPSY FORCEPS

[75] Inventors: Robert F. Bencini, Dracut; Barry D. Weitzner, Chelmsford, both of Mass.

[73] Assignee: C. R. Bard, Inc., Murray Hill, N.J.

[21] Appl. No.: 583,617

[22] Filed: Sep. 17, 1990

Related U.S. Application Data

[63] Continuation-in-part of Ser. No. 304,367, Jan. 31, 1989, abandoned.

[51] Int. Cl.⁵ ............................................. A61B 10/00
[52] U.S. Cl. ............................ 128/751; 606/206; 606/207
[58] Field of Search .................... 606/205–208, 606/113, 170, 106, 144, 148, 171; 128/751, 752

[56] References Cited

U.S. PATENT DOCUMENTS

| | | | |
|---|---|---|---|
| 2,060,366 | 11/1936 | Dunlap | 119/154 |
| 2,113,246 | 4/1938 | Wappler | 128/321 |
| 2,518,994 | 8/1950 | Miller | 128/321 |
| 3,147,749 | 9/1964 | Marsh | 128/2 |
| 3,506,012 | 4/1970 | Brown | 128/346 |
| 3,628,522 | 9/1970 | Kato | 128/2 |
| 3,895,636 | 7/1975 | Schmidt | 128/305 |
| 3,924,608 | 9/1975 | Mitsui | 128/2 |
| 4,174,715 | 11/1979 | Hasson | 128/321 |
| 4,200,111 | 4/1980 | Harris | 128/751 |
| 4,427,014 | 1/1984 | Bel et al. | 128/751 |
| 4,449,518 | 5/1984 | Konomura et al. | 128/4 |
| 4,506,669 | 3/1985 | Blake, III | 128/334 |
| 4,522,206 | 6/1985 | Whipple et al. | 128/312 |
| 4,526,172 | 7/1985 | Stephenson | 606/208 |
| 4,646,751 | 3/1987 | Maslanka | 128/751 |
| 4,655,219 | 4/1987 | Petruzzi | 128/321 |
| 4,669,471 | 6/1987 | Hayashi | 128/321 |
| 4,686,965 | 8/1987 | Bonnet et al. | 128/4 |
| 4,721,116 | 1/1988 | Schintgen et al. | 128/751 |
| 4,763,668 | 8/1988 | Macek et al. | 606/206 X |
| 4,815,476 | 3/1989 | Clossick | 128/751 |
| 4,817,630 | 4/1989 | Schintgen et al. | 128/751 |
| 4,881,550 | 11/1989 | Kothe | 128/752 |

FOREIGN PATENT DOCUMENTS 140951 4/1961 U.S.S.R. .
1427397 3/1976 United Kingdom ............... 606/206

Primary Examiner—Michael H. Thaler
Attorney, Agent, or Firm—Wolf, Greenfield & Sacks

[57] ABSTRACT

A disposable biopsy forceps includes an elongate tubular member having proximal and distal ends. Manually operated actuating means is mounted to the proximal end of the flexible tubular member. A biopsy jaw assembly is mounted to the distal end of the tubular member and is operatively connected to the actuating means by a control wire extending through the tubular member. Several embodiments of jaw arrangements are disclosed. At least the cups and cutting rim portion of the cutting jaws retain an edge sufficiently sharp to cut tissue.

15 Claims, 9 Drawing Sheets

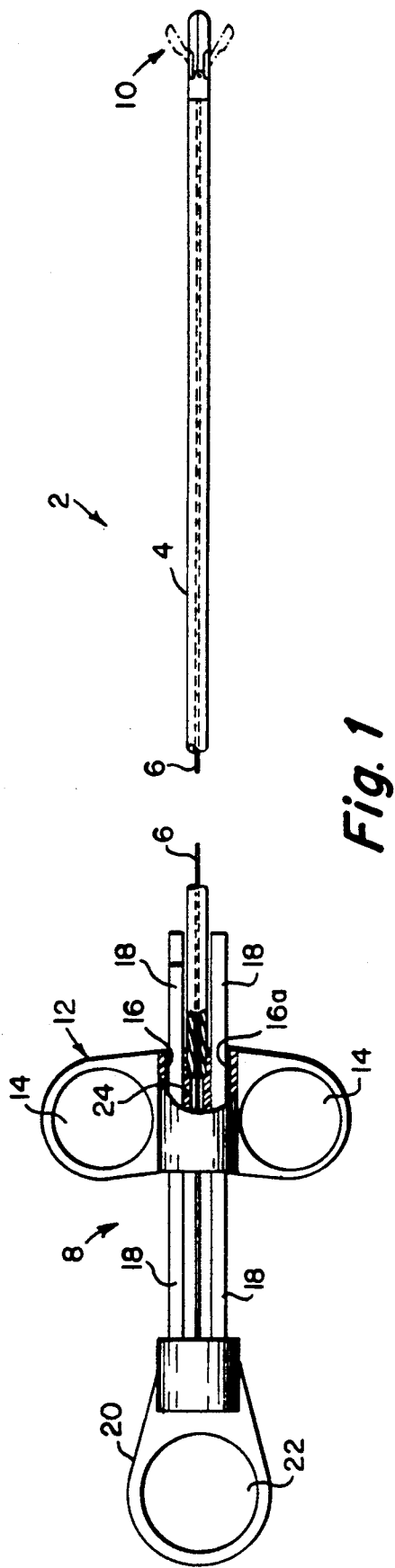
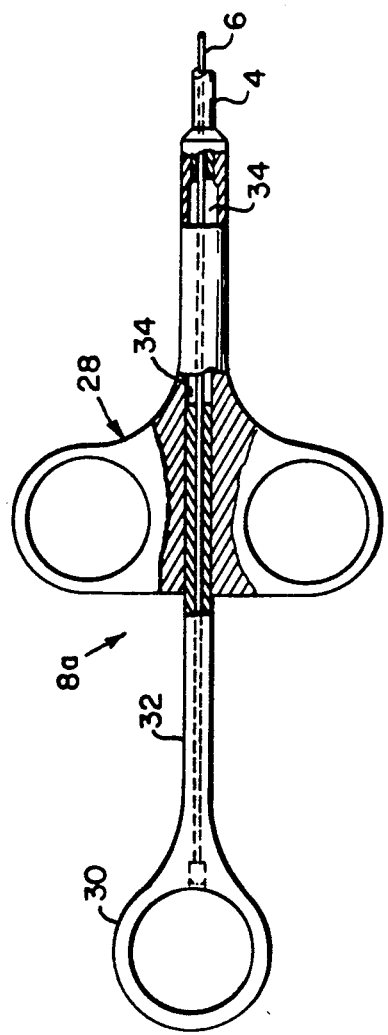
Fig. 1
Fig. 2

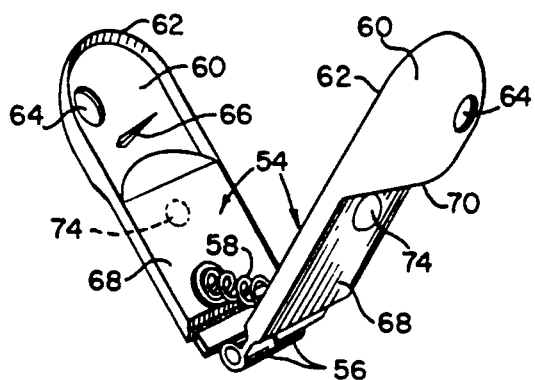
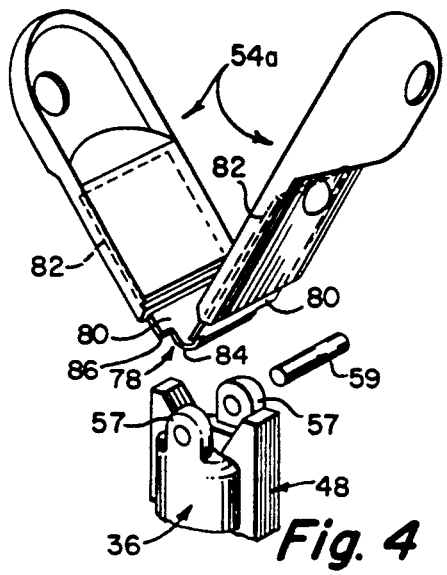
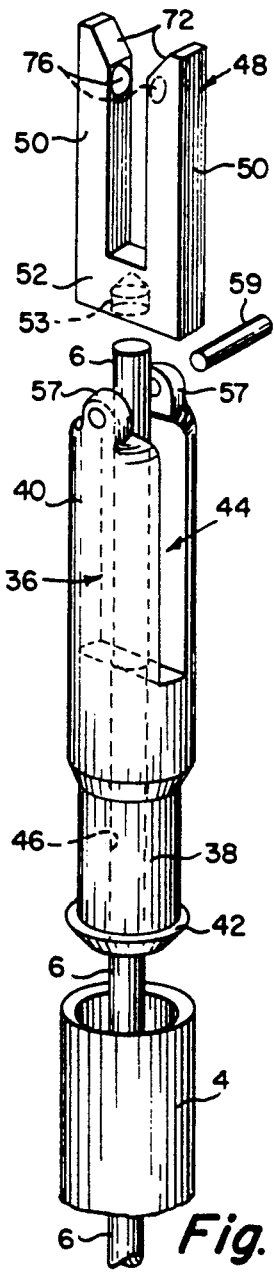
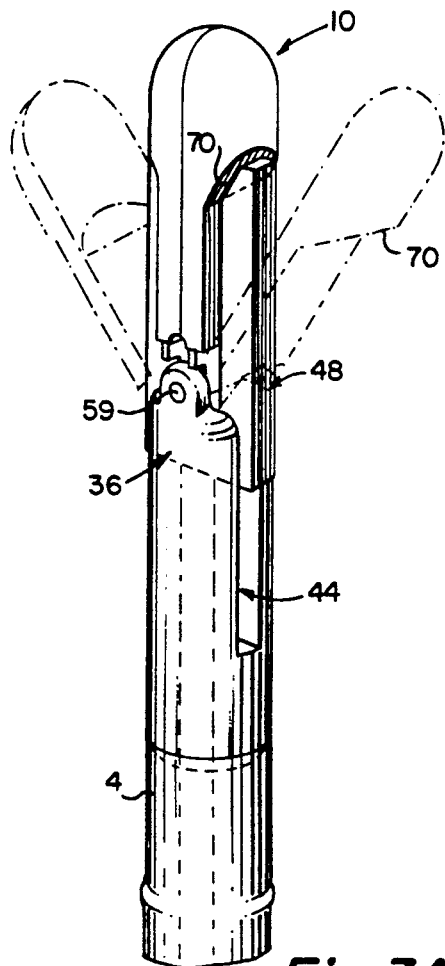
Fig. 3
Fig. 4
Fig. 3A

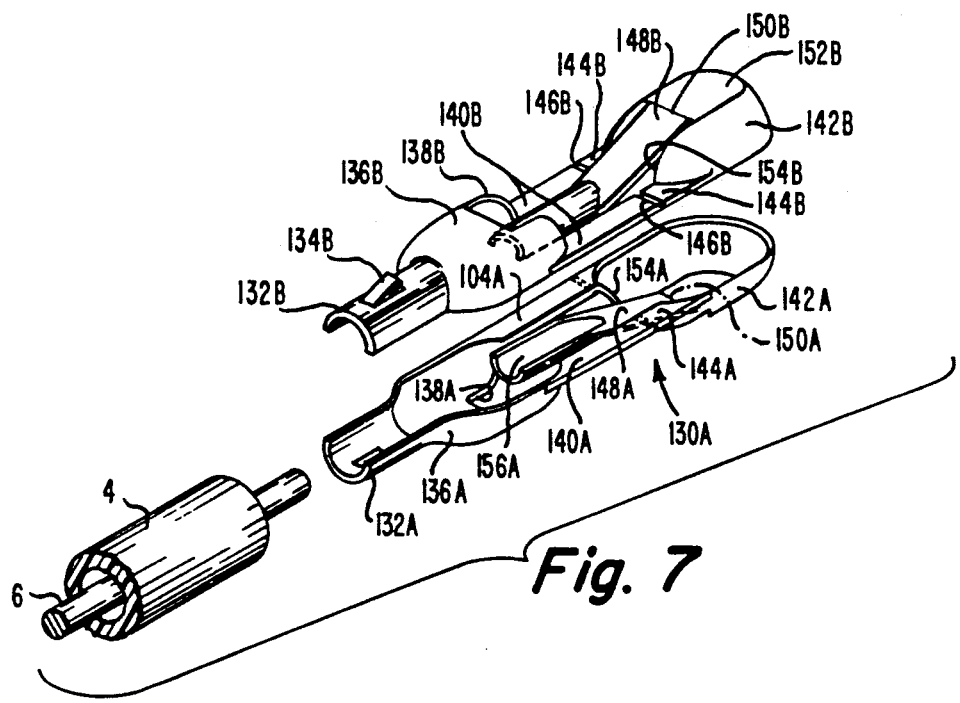
Fig. 7
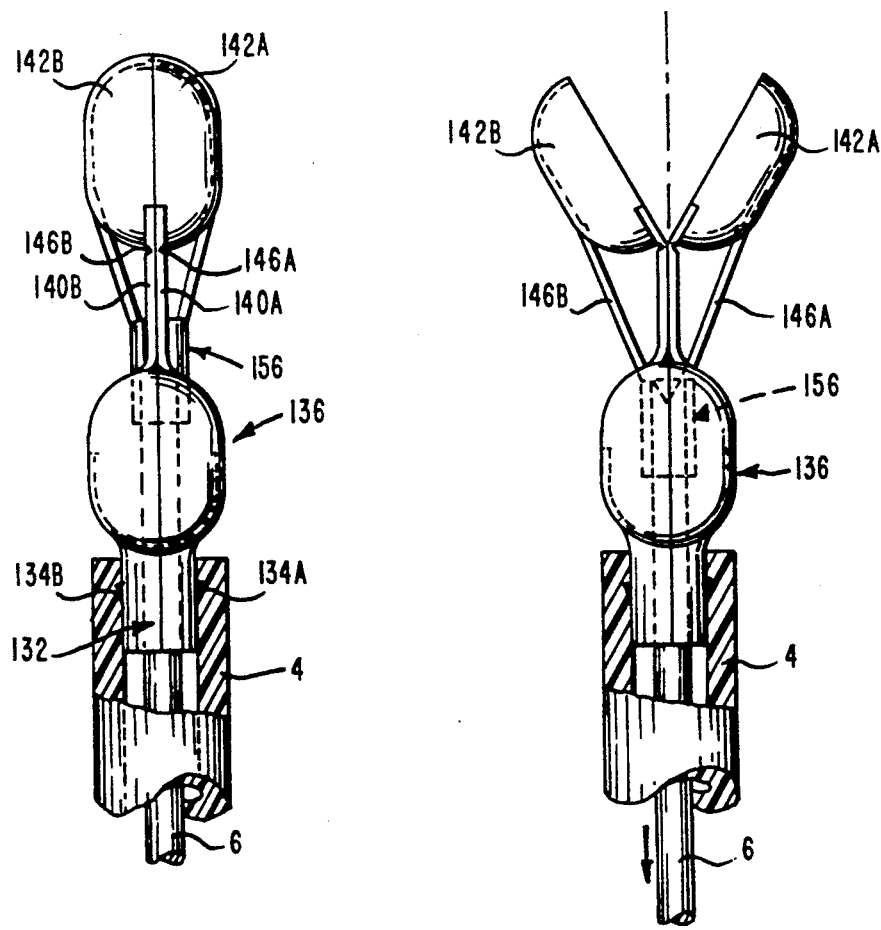
Fig. 7B  Fig. 7A

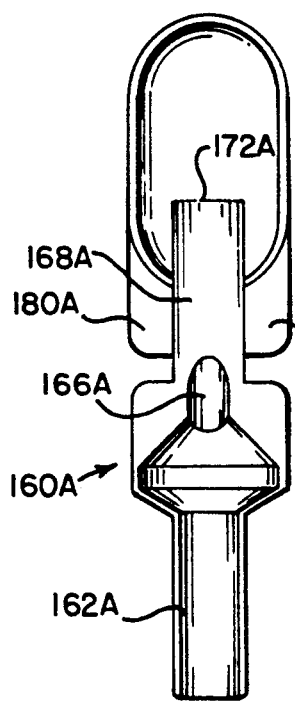
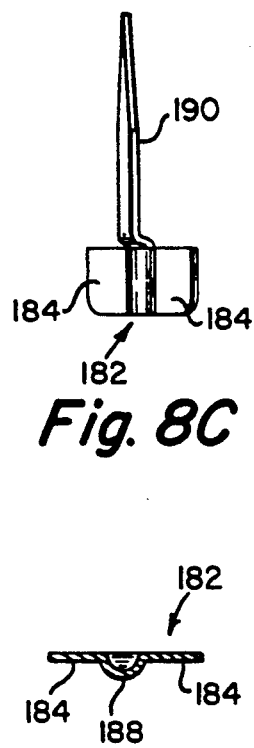
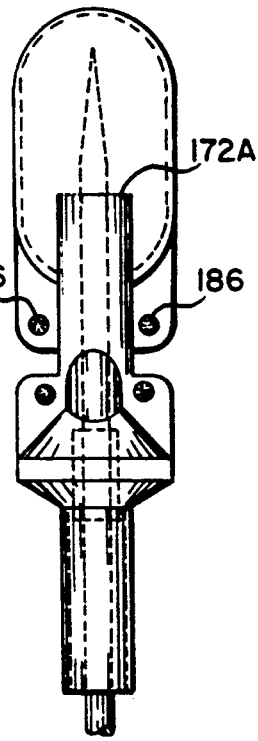
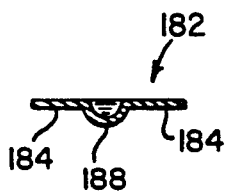
Fig. 8A
Fig. 8C
Fig. 8D Fig. 8B
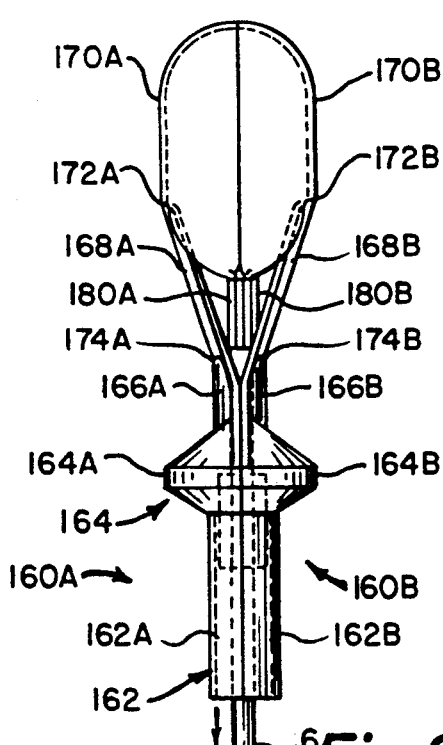
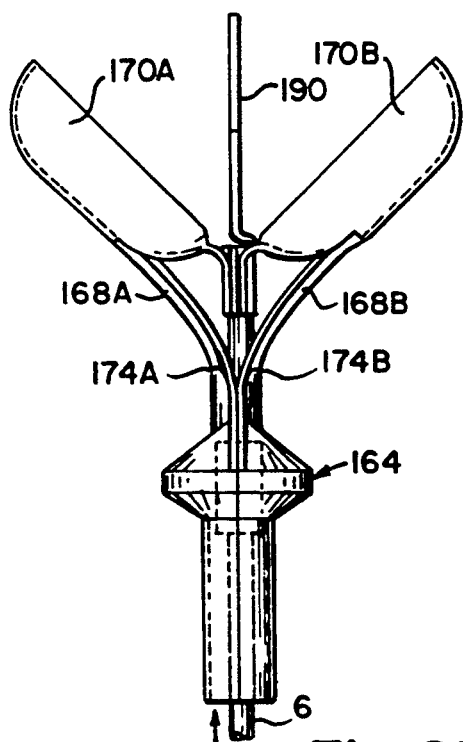
Fig. 8E
Fig. 8F

DISPOSABLE BIOPSY FORCEPS

RELATED APPLICATION

This application is a continuation-in-part of pending application Ser. No. 304,367 filed Jan. 31, 1989 now abandoned.

FIELD OF THE INVENTION

The invention relates to biopsy forceps for taking small internal tissue samples from a patient.

BACKGROUND OF THE INVENTION

When making an endoscopic examination of a particular site in a patient's body, it is common for the physician to take at least one tissue sample from that site for analysis. A variety of such devices for taking of small tissue samples are in use. In general, such biopsy devices include a small diameter elongate catheter-like instrument adapted to be passed through a lumen in the endoscope, the device being longer than the endoscope so that its distal end can extend out of the distal end of the endoscope. The distal end of the device typically is provided with a pair of sharp jaws that can be open and closed to cut away a small sample of tissue to be investigated. The opening and closing of the jaws is controlled manually by the physician by manipulating controls at the proximal end of the device.

Such endoscopic biopsy procedures involve repeated insertion and removal of the device through the narrow endoscope channel when it is necessary to take multiple biopsies. The device must be sufficiently rugged to withstand such repeated use yet must be constructed so that it will not cause damage to any of the parts of the endoscope as it is advanced through the endoscopic channel.

Among the difficulties presented with such devices is that they typically are relatively expensive, partly because of the intricate work required to manufacture the miniature jaws and jaw actuating mechanisms. Additionally, the cutting edges of the jaw tend to become dull with use and require periodic sharpening, a procedure that involves considerable skill and a high degree of care because of the miniature size of the jaws. Very slight errors in sharpening procedure can impair seriously the effectiveness of the jaws. Often, it is only possible to sharpen such a device a few times before its dimensions are so changed that it is no longer effective. When that occurs, it is common practice to replace the entire device. Also among the difficulties presented by such endoscopic biopsy devices is that they are difficult to clean and sterilize. The jaw mechanisms define numerous crevices. Additionally, the elongate body of the device is made from a highly flexible tightly wound helical coil which provides numerous crevices for retaining debris or contaminants and the like.

It is believed that there is a need for a low cost, simple, disposable endoscopic biopsy device. It is among the general objects of the invention to satisfy that need.

SUMMARY OF THE INVENTION

In several of the embodiments of the invention, the device includes an elongate flexible solid wall tubular catheter formed from a plastic extrusion. A control wire extends through the catheter and is connected at its proximal end to an actuation means by which the physician may pull or push on the wire. The distal end of the device carries a pair of jaws each of which has at its end a sharp rimmed cup so that when the jaws are brought together, they may sever and retain a sample of tissue. Unlike the prior art biopsy devices, the embodiments of the present invention are free of complex linkages and multiple hinge points, the present invention incorporating either a single hinge point or a living hinge for mounting the jaws. In another embodiment, the jaws and associated actuating means are formed to include a number of flexible living hinges removably mounting the jaws as well as for actuating the jaws. In each embodiment, the jaws are caused to close by a longitudinally movable jaw actuator that is operated by the control wire. In each embodiment, the jaw actuator engages the jaws to cause the jaws to close as the actuator moves in a distal direction. When the jaw actuator is retracted in a proximal direction, the jaws, which are biased in an open configuration, are permitted to open.

In two of the embodiments of the invention the jaws are connected by a single hinge pin and are biased apart by a spring. In another embodiment of the invention, the jaws are hinged together by a strip of spring metal. In another embodiment of the invention, the jaws are molded from plastic in a single integral unit which defines a living hinge between the jaws. In still another embodiment of the invention, the jaws, their support and the actuating means are formed in a single unitary piece in which relatively movable elements are hinged together by a living hinge. The latter embodiment may be stamped from thin spring metal.

It is among the general objects of the invention to provide endoscopic biopsy devices having biopsy jaw arrangements that are of relatively simple inexpensive design.

Another object of the invention is to provide endoscopic biopsy devices of sufficiently low cost as to be disposable yet which may be reused if desired and, if reused, may be easily cleaned and sterilized.

A further object of the invention is to provide endoscopic biopsy devices having simplified, positive means for opening and closing its jaws.

Another object of the invention is to provide endoscopic biopsy devices in which the jaws, when closed, remain in the closed position until opened by the user.

DESCRIPTION OF THE DRAWINGS

The foregoing and other objects and advantages of the invention will be appreciated more fully from the following further description thereof, with reference to the accompanying drawings wherein:

FIG. 1 is a fragmented partly broken away illustration of one embodiment of an endoscopic biopsy device in accordance with the present invention;

FIG. 2 is a fragmented sectional illustration of the proximal end of an endoscopic biopsy device showing an alternative construction for the actuating means;

FIG. 3 is an exploded enlarged view of the distal end of the biopsy jaws and jaw actuator mechanism in accordance with one embodiment of the invention;

FIG. 3A is an enlarged illustration of the assembled device of FIG. 3 showing the jaws in closed position in solid lines and in the open position in phantom;

FIG. 4 is an exploded enlarged illustration of another embodiment of the biopsy jaws which the jaws are hinged together by a leaf spring;

FIG. 7 is an exploded, enlarged illustration of another biopsy jaw configuration in accordance with another embodiment of the invention;

FIG. 7A is a side elevation of the assembled jaws of FIG. 7 illustrating the jaws in an open configuration;

FIG. 7B is an enlarged side view of the jaws of FIG. 7 in a closed configuration;

FIGS. 8A-8E illustrate another embodiment of the invention in which FIG. 8A is an illustration of the inwardly facing side of one of the halves of the device, FIG. 8B is a view of the outwardly facing side of one of the halves of the device, FIG. 8C is an illustration of an integral connector element and retention spike, FIG. 8D is an illustration of the connector element of FIG. 8C as seen from the bottom of FIG. 8C, FIG. 8E is an illustration of the assembled device in its closed position and FIG. 8F is an illustration of the assembled device in its open position;

FIGS. 9A-9E illustrate another embodiment of the invention in which FIG. 9A is an illustration of the inwardly facing side of one of the halves of the device, FIG. 9B is a view of the outwardly facing side of one of the halves of the device, FIG. 9C is an illustration of the connection between the pull wire and the jaws, FIG. 9D is an illustration of the assembled device in its closed position and FIG. 9E is an illustration of the assembled device in its open position; and FIGS. 10A-10F illustrate another embodiment of the invention in which FIG. 10A is an illustration of the inwardly facing side of one of the halves of the device, FIG. 10B is a view of the outwardly facing side of one of the halves of the device, FIG. 10C is a bottom view, partly in section, of one of the jaw halves as seen along the line 10C-10C of FIG. 10A, FIG. 10D is an illustration of the connector element and retention spike, FIG. 10E is an illustration of the assembled device in its closed position and FIG. 10F is an illustration of the assembled device in its open position.

DESCRIPTION OF THE ILLUSTRATIVE EMBODIMENTS

Figure 5:
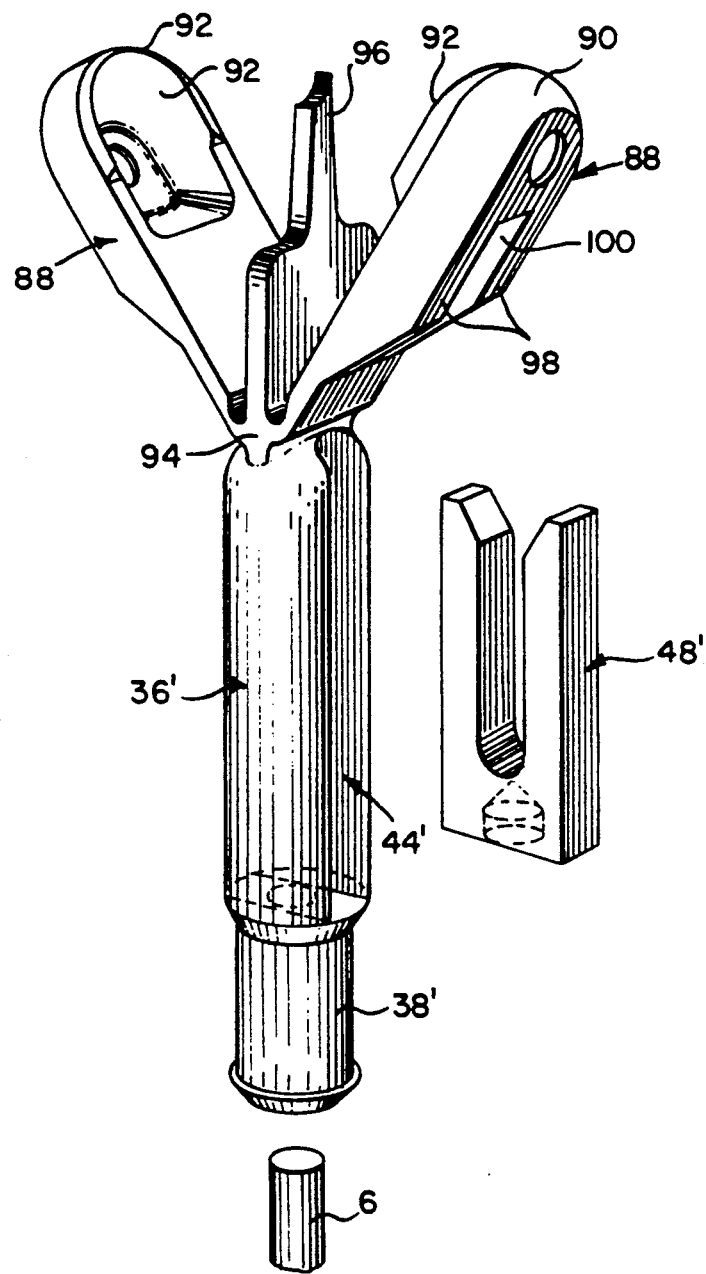
FIG. 5 is an exploded enlarged view of a biopsy jaw element in accordance with another embodiment of the invention in which the jaws are molded together from plastic and are hinged together by a living hinge.

FIG. 1 shows one embodiment of the invention in which an elongate endoscopic biopsy device 2 includes an elongate flexible plastic tube 4. The tube 4 is formed preferably from polypropylene or other suitable plastic which will resist longitudinal stretching as a result of the axial loads applied to it by operation of the jaw. A control wire 6 which may be formed from stainless steel extends through the lumen in the plastic tube 4. The control wire 6 connects to an actuating means 8 at the proximal end of the device by which the physician controls the device. A pair of biopsy jaws 10 is mounted to the distal end of the plastic tube 4. The jaws 10 are operatively associated with the control wire 6 so that they may be closed or opened (as illustrated in phantom in FIG. 1) by operation of the control wire 6. When the jaws 10 are closed they define a diameter substantially the same as the tube 4 so that the entire device will fit slidably through the channel in the endoscope. The dimensions of the channel in the endoscope will vary for different types of endoscopes. For example, endoscopes used in gastrointestinal environments typically have a biopsy channel 2.8 mm in diameter whereas endoscopes for pulmonary use typically have a biopsy channel 2.0 mm in diameter. Additionally, the lengths of such endoscopes varies according to their use. Pulmonary endoscopes are shorter than gastrointestinal endoscopes. By way of further example, the tube 4 of the present invention may be of the order of between 0.070" to 0.080" in diameter and may be between 100 cm to 240 cm in length, depending on the type and size of the endoscope with which it is to be used. Other lengths and diameters may be appropriate for other types of endoscopes which may have different lengths and channel sizes. It may be desirable, in use, to coat the outer surface of the tube 4 with a lubricious material. The diameter of the control wire 6 depends on the length of the device and, possibly, on the type of tissue which the device will be used to sample. The stiffness of the control wire is a function of its diameter. Preferably, the control wire usable for the particular type of endoscope should be the smallest diameter that will operate the jaws 10 so as not to adversely affect the flexibility of the device. By way of example, we have found that a control wire as small as 0.016" diameter may be effective to operate the jaws in a device 100 cm to 240 cm long. The control wire preferably is coated with Teflon (polytetrafluoroethylene) to enhance its ability to slide in the tube 4.

In the embodiment shown in FIG. 1, the actuating means 8 includes a stationary member 12 that is attached to the proximal end of the plastic tube 4. The stationary member 12 preferably is provided with a pair of finger holes 14. The stationary member 12 also is provided with a pair of longitudinally extending bores 16 which slidably receive a pair of rods 18. A thumb member 20 having a thumb hole 22 is attached to the proximal ends of the parallel rods 18. The proximal end of the pull wire 6 extends through an opening 24 in the stationary member 12 and is attached, at its proximal end, to the thumb member 20. From the foregoing, it will be appreciated that the proximal end of the biopsy device 2 can be operated with one hand, to pull the pull wire 6 proximally or push it distally. The distal end of the pull wire is connected to the biopsy jaws 10 in a manner described further below.

FIG. 2 illustrates an alternate actuating means 8 at the proximal end of the device. The actuating means 8 also includes a stationary member 28 and a thumb member 30. The thumb member 30 is disposed at the proximal end of a rod 32 which is slidably received within a bore 34 of the stationary member 28. The control wire 6 is connected at its proximal end to the thumb member 30 and extends distally through the bore 34 in the stationary member 28. The proximal end of the catheter tube 4 is secured in the distal end of the bore 34, the control wire 6 extending through the tube 4 as described above in connection with FIG. 1.

FIGS. 3 and 3A illustrate one embodiment of the biopsy jaw assembly. The assembly includes a generally cylindrical jaw support 36 having a proximal end 38 that fits securely within and may be adhesively attached to the distal end of the tube 4, and a distal cylindrical end 40. The proximal end of the jaw support 36 is of reduced diameter to fit within the lumen of the plastic tube 4 and may be provided with a barb-like circumferential flange 42 at its most proximal end which may securely engage and tend to dig into the inner surface of the lumen in the plastic tube 4 thereby to secure the jaw support in place. The distal end 40 of the jaw support 36 has a longitudinally extending slot 44. The inner end of the slot 44 communicates with the longitudinally extending bore 46 formed centrally through the proximal end 38 of the jaw support 36. The distal end of the control wire 6 extends through the bore 46 and into the slot 44 where it is connected to a jaw actuator 48. In this embodiment of the invention, the jaw actuator 48 is U-shaped having a pair of longitudinally extending spaced fingers 50 connected at a base 52. The base 52 has a proximally extending socket 53 in it bottom which receives the distal end of the control wire 6. The control wire 6 and base 52 may be secured together by brazing. The width of the jaw actuator 48 is such that it is slidably received within the longitudinal slot 44 of the jaw support 36. As will be described in further detail, the jaw actuator 48 may be reciprocated within the slot 44 to open and close the biopsy jaws. The jaw support 36 and jaw actuator 48 may be formed from an appropriate metal such as a surgical grade stainless steel.

As shown in FIGS. 3 and 4, the biopsy jaws include a pair of jaw members 54 which are preferably injection molded from a suitable plastic. The plastic should be capable of being molded to define and retain sharp cutting edges. We have found a suitable polymeric material commercially available from Du Pont under the 500 series Delrin polyoxymethylene, polyacetol. Alternately, the jaws 54 may be injection molded from a powdered metal in a scintering process. Parts made in such a process can be obtained for example, from Advanced Forming Technology, Inc., of Longmont, Colo. The proximal ends of the jaw members 54 are provided with hinge elements 56. Jaw elements 54 are biased apart by a spring 58. The distal, outer, free ends of the jaw members are formed to define hollow cups 60 having inwardly facing sharp edges 62. The jaw members 54 are mounted by their hinge elements 56 to trunions 57 at the distal end of the jaw support 36 on opposite sides of the slot 44. A hinge pin 59 extends through the trunions 57 and the hinge elements 56.

When the jaw members 54 swing together, their sharp edges 62 meet with the cups 60 combining to enclose whatever tissue may have been severed and entrapped between the cups 60. The cups 60 may be provided with drain holes 64 to permit liquid to drain off. Barbs 66 may be formed on the inner surface of the cups 60 to further securely retain tissue entrapped between the cups 60.

The proximal portions 68 of the jaw members 54 are dimensioned so that they can be contained between the fingers 50 of the jaw actuator 48 when the jaw members 54 are brought together. Thus, as shown in solid in FIG. 3A, when the jaw actuator 48 is advanced distally, by operation of the control wire 6, the fingers 50 of the jaw actuator 48 engage the outwardly facing surfaces of the proximal portions 68 of the jaw members 54 so that continued distal advancement of the jaw actuator 48 will cause the jaws 54 to swing to a closed position as shown in solid in FIG. 3A. In the embodiment shown in FIGS. 3 and 3A, a portion 70 of the outwardly facing surface of the cups 60 is beveled and defines a stop against which a similarly beveled surface 70 on the ends of the fingers 50 can bear. Engagement of the beveled ends 72 of the fingers 50 with the beveled surfaces 70 on the cups 60 serves to stop the distal advancement of the jaw actuator 48, the jaw members 54 being in their fully closed position. It will be appreciated from FIG. 3A that when the jaw actuator and jaws are in this position, the jaw members 54 are securely contained between the fingers 50 which lock the jaws in a closed position.

In order to provide a further latching effect, as well as to provide a distinct feel for the physician to confirm full closure of the jaw members 54, a dimple 74 may be formed in the outwardly facing surface of each of the jaw members, each of the dimples 74 being adapted to receive a protrusion 76 formed near the outer ends of each of the fingers. The fingers 50 are sufficiently resilient so that they may spread apart to permit the protrusions 76 to slide along the outwardly facing surfaces of the proximal portions 68 of the jaw members 54. When the protrusions 76 engage the dimples 74, they do so in somewhat of a snap fit that can be detected at the actuating means 8 by the physician to provide confirmation that the jaws are closed and locked.

FIG. 4 illustrates a modified embodiment of the jaw assembly. In this embodiment, the jaw members 54 are hinged together by a one piece leaf spring hinge 78. The spring metal hinge 78 includes tongues 80 that are received in slots 82 formed in the jaw members 54. The jaw members 54 may be injection molded from plastic or metal with the tongues 80 being molded into the jaw members 54. The mid-portion of the leaf spring 78 is of reduced width so that it can fit between the trunions 57 of jaw support 36. The juncture of the tongues 80 with the central portion 84 of the leaf spring 78 defines a shoulder 86 which overlaps the trunions 57. The jaw arrangement of FIG. 4 is retained between the trunions by hinge pin 59 which overlies the central portion 84 of the leaf spring 78 and is supported by the trunions 57. The actuation of the embodiment shown in FIG. 4 is the same as that described above in connection with the embodiment of FIG. 3.

Figure 5A:
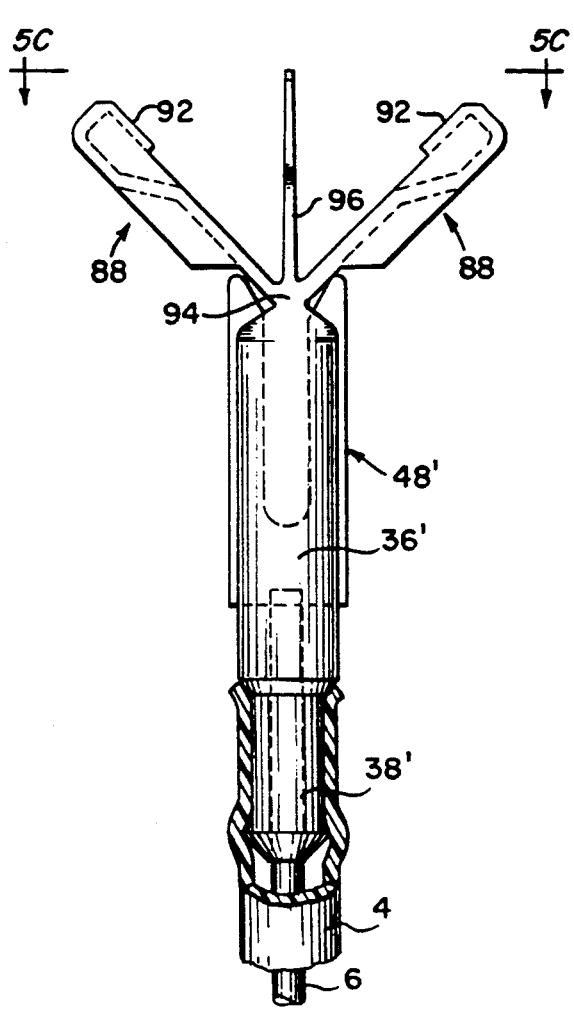
FIG. 5A is an enlarged side view of the assembled device of FIG. 5 illustrating the jaws in an open configuration.

FIG. 5 shows another embodiment of the invention in which the jaws 88 and jaw support 36' are molded from a suitable plastic such as Delrin, in a single piece. In this embodiment of the invention, the cylindrical jaw support 36' and longitudinal slot 44' are of the same configuration as described above in connection with the embodiment of FIG. 3 except that it is injection molded from plastic integrally with the jaw members 88. In this embodiment, no hinge pins or trunions are utilized, the jaw members 88 being molded integrally with the jaw support 36'. The jaw members 88 are molded to include cups 90 having sharp cutting edges 92 which function in the same manner as described above with the embodiments of FIG. 3. The jaw members 88 are molded integrally with jaw support 36' and are attached to the distal end of the jaw support 36' at a common juncture 94. The thickness of the plastic material adjacent the common juncture is controlled so as to define a resilient living hinge which will normally bias the jaw members 88 in an open configuration as shown in FIGS. 5 and 5A. In this embodiment of the invention, a distally extending spike 96 may be molded integrally with the jaw members 88 extending distally from the common juncture 94. The spike 96 serves to further secure a tissue sample captured between the cups 90, serving a function similar to that of the barbs 66 in the embodiment shown in FIG. 3.

The slot 44' receives the jaw actuator 48' in the same manner as corresponding elements in the embodiment described in FIG. 3. In this embodiment, the jaw members 88 may be provided with stiffening ribs 98 on opposite sides of the region engaged by the jaw actuator 48'. The stiffening ribs 98 define a slot 100 which receives the fingers of the jaw actuator 48'.

FIG. 5A illustrates the embodiment of FIG. 5 with the jaw actuator 48' in its proximal, retracted position and with the jaw members 88 in their open position. When the jaw members 88 are open, the spike 96 will be exposed. The spike 96 may be used to stabilize the distal end of the device in tissue to be sampled. The spike 96 also may serve as a skewer to pass through and retain cut tissue samples while the biopsy device continues to take additional tissue samples.

Figure 5B:
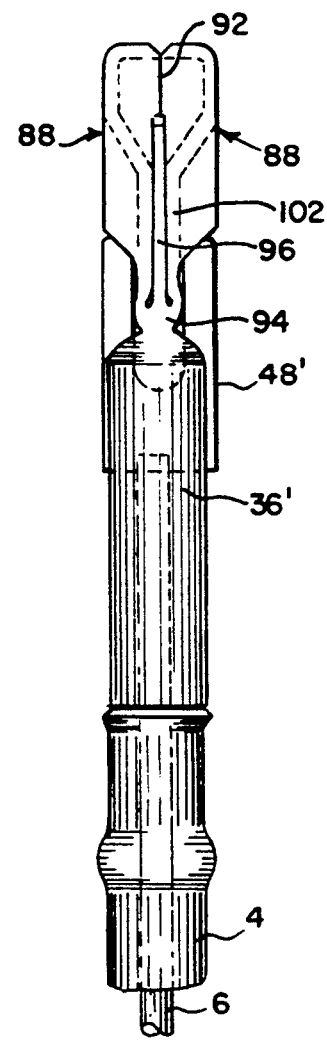
FIG. 5B is an enlarged illustration of the device of FIG. 5 showing the jaws in closed configuration.
Figure 5C:
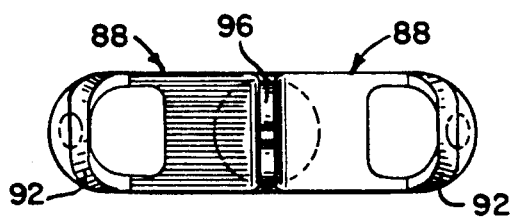
FIG. 5C is an enlarged top view of the jaws of FIG. 5A.

FIG. 5B illustrates the configuration of the device with the actuator 48' extended distally to draw the jaw members 88 together. It may be noted that in this embodiment, the parts are molded so that a clearance is left between the proximal portions 102 of the jaw members 88 so that they do not interfere with the central spike 96. The cutting edges 92 are raised somewhat so that they will engage each other and effect a complete severing of tissue. The one piece molded embodiment of FIG. 5 is formed from a plastic that is relatively hard and capable of defining a good cutting edge 92 such as Delrin, described above. The Delrin material has a suitable combination of properties necessary to form a sharp cutting edge as well as to provide the resiliency required for the living hinge. We have found that a jaw assembly molded in a single piece from Delrin has good elastic memory retention during at least thirty opening and closing cycles of the jaws which is well in excess of the normally required number of openings and closing cycles that can be expected with a single patient.

Figure 6:
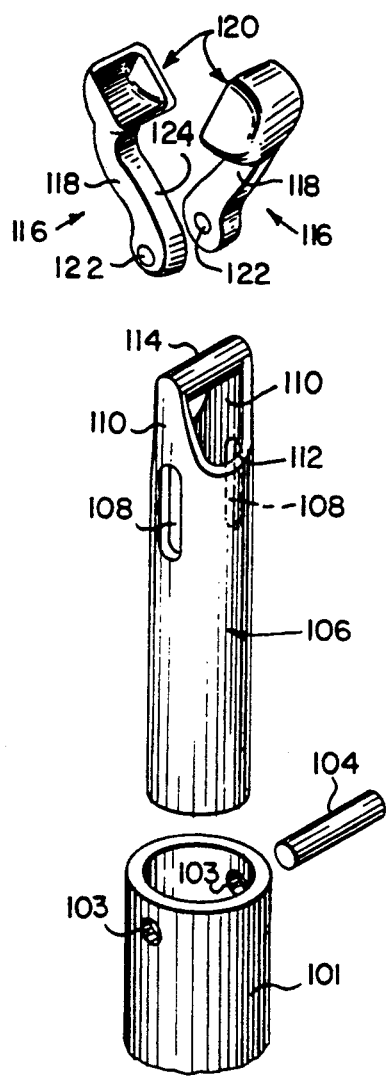
FIG. 6 is an exploded, enlarged view of a biopsy jaw configuration in accordance with another embodiment of the invention.
Figure 6A:
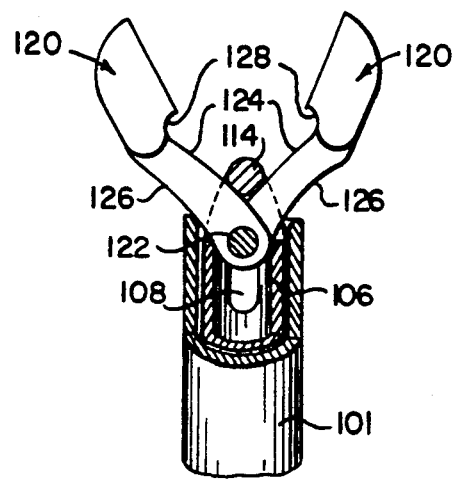
FIG. 6A is an enlarged side view of the assembled jaws of FIG. 6 showing the jaws in an open configuration.
Figure 6B:
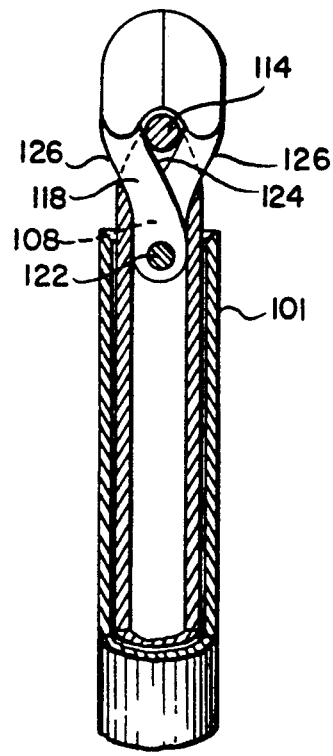
FIG. 6B is an enlarged side view of the jaws of FIG. 6 in closed configuration.
Figures 9A, 9B, 9C:
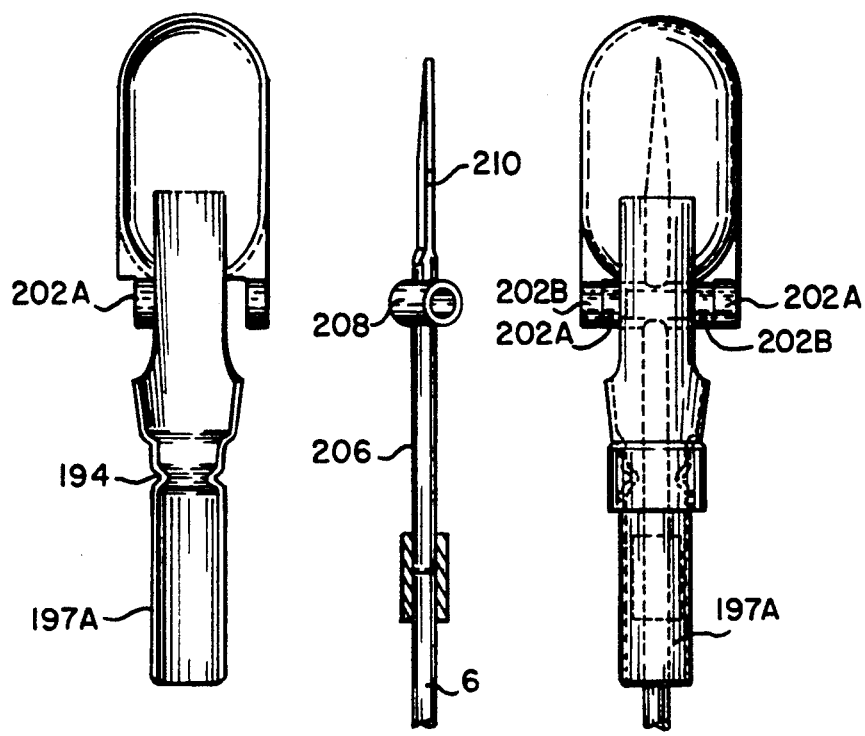
Figures 9D, 9E:
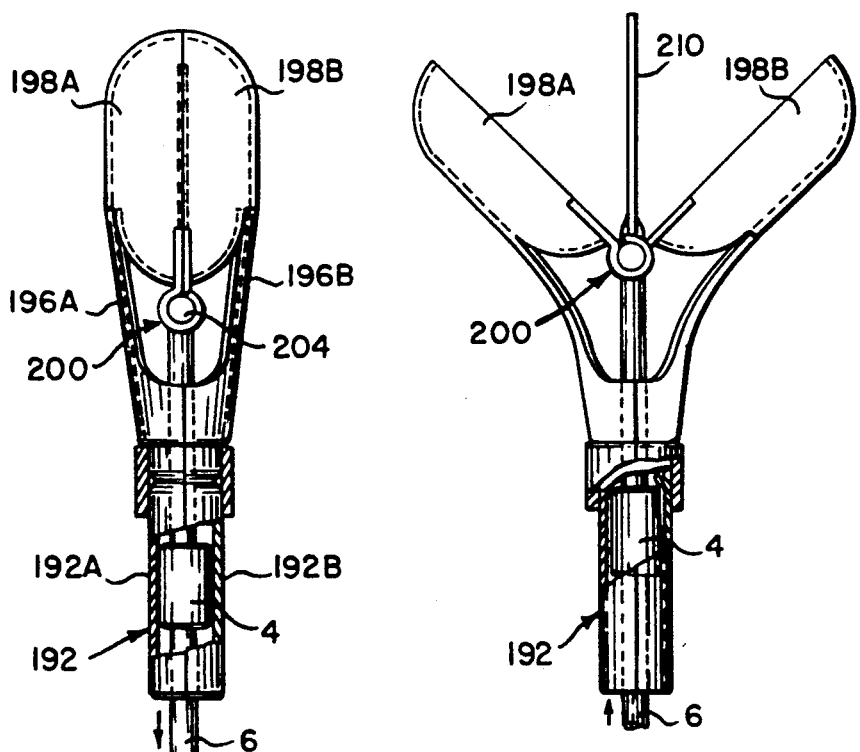

FIGS. 6, 6A and 6B illustrate another embodiment of the invention. In this embodiment a rigid tubular housing 100 is attached to the distal end of the tube 4 in the same manner as in the other embodiments. The housing 100 may be formed from plastic or metal, as desired. The housing 100 has a pair of diametrally opposed holes 102 formed at its distal end which are adapted to receive a pin 104. A tubular actuating member 106 is disposed slidably within the housing 100. The proximal end of the tubular actuating member 106 is secured to the distal end of the control wire 6 (not shown) as by brazing, soldering, suitable adhesive or the like. The actuating member 106 has a pair of diametrally opposed longitudinally extending slots 108 arranged to receive the pin 104. The slots 108 and pin 104 cooperate t limit the proximal and distal extremities of motion permitted to the actuator 106. The distal end of the actuator 106 includes a pair of distally extending projections 110 aligned with the slots 108. The cutouts 112 between the projection 110 are cut away to define openings through which the arms of a pair of jaws may extend. The outermost ends of the projections 110 are connected by a transverse bar 114.

A pair of biopsy jaws 116 having arms 118, cutting cups 120 at one end and pivot holes 122 at the other end are attached to the distal end of the device. The jaws 116 may be injection molded from a suitable plastic material such as Delrin or from powdered metal. As shown more clearly in FIGS. 6A and 6B, the proximal ends of the arms 118 are pivotably attached to the pin 104 by the holes 122. The arms 118 of the jaws 116 extend through the cutouts 112 and on opposite sides of the bar 114. As shown in FIG. 6A when the actuating member 106 is drawn proximally by pulling on the control wire 6, the bar 114 which extends between the arms 118 of the jaws 116 engages the inwardly facing surfaces 124 of the arms 118 to urge the arms 118 apart, thereby opening the jaws. When it is desired to close the jaws to cut a biopsy sample, the control wire is urged distally to move the actuator member 106 to the configuration illustrated in FIG. 6B. As the device advances from the configuration of FIG. 6A to that of FIG. 6B the bar 114 moves distally out of the way while the edges of the cutouts 112 move distally and engage the outwardly facing surfaces 126 of the arms 118. In doing so, the actuating member 106 urges the arms 118 together to close the jaws 116 in a cutting action. When the jaws 116 are closed, the bar 114 extends through a space defined by the recessed regions 128 of the arms 118, just proximal of the cutting cups 120. When in the closed configuration, the pin 104 is bottomed out against the proximal end of the slot 108. When the cups are in their most open position, the pin 104 is bottomed against the most distal end of the slot 108.

FIGS. 7, 7A and 7B illustrate another embodiment of the invention. In this embodiment, the biopsy jaws, their supporting elements and actuating means may be formed from two identical elements stamped from sheet material such as suitable spring metal. The identical halves are joined to form a complete biopsy jaw device which is mountable to the distal end of the elongate flexible plastic tubular shaft. More particularly, as shown in FIGS. 7, 7A and 7B, the device includes a pair of identical halves 130A, 130B, each of which may be stamped from a thin sheet of spring metal such as 0.005" spring steel. The halves 130A, 130B may be formed by conventional stamping techniques. Each of the halves is formed to include a proximal tube section 132A, 132B which, when the halves 130A, 130B are mated, will define a proximal tube 132 that is insertable into the distal end of the tube 4. Each of the tubular sections 132A, 132B is formed with a projecting barb 134A, 134B which will engage the inner surface of the tube 4 to secure the assembly to the tube 4. The proximal tube sections 132A, 132B each merge into an enlarged, somewhat bulbous, body portion 136A, 136B which, when the halves are joined will define a bulbous hollow body 136. Openings 138A, 138B are formed in the upper portion of each of the body segments 136A, 136B to receive a portion of the actuating mechanism that will be described. Extending from the distal portion of each of the body segments 136A, 136B, and on opposite sides of their associated openings 138A, 138B is a pair of distally extending, transversely spaced cup support struts 140A, 140B. The biopsy jaws 142A, 142B are hingedly attached to the distal ends of the pairs of support struts 140A, 140B by a pair of jaw supports 144A, 144B. The pairs of jaws supports 144A, 144B are hinged to the distal ends of their associated support struts 140A, 140B at a living hinge line 146A, 146B. The hinge lines 146A, 146B may be formed by direct stamping in the juncture of the support struts 140A, 140B and the jaw supports 144A, 144B. As will be appreciated with reference to FIGS. 7A and 7B, when the halves 130A and 130B are joined, the facing support struts 140A and 140B will be secured together, as by spot welding, while the jaw supports 144A, 144B remain unattached to each other so that they may pivot between open and closed positions as suggested in FIG. 7A and 7B, respectively. Preferably, the support struts 140A, 140B and their associated jaw supports 144A, 144B are arranged so that when the control wire is pulled in a proximal direction (as will be described), the jaw supports 144 will be urged apart, as suggested in FIG. 7A, thereby opening the biopsy jaws 142.

In order to open and close the biopsy jaws 142, each of the jaws is formed to include an integral actuator strut 148A, 148B. The distal end of each actuator strut 148A, 148B is hingedly attached, at a living hinge line 150A, 150B, to the bottom wall 152A, 152B of its associated biopsy jaw 142A, 142B. As will be apparent, limited movement between the actuator struts 148A, 148B and their associated biopsy jaws 142A, 142B is permitted by an opening 154A, 154B formed on the proximal portion of each of the biopsy jaws. The actuator struts 148A, 148B pass partially through the openings 154A, 154B. The proximal ends of the actuator struts 148A, 148B are attached to semitubular elements 156A, 156B which, when joined, form a tubular connector 156. As illustrated in FIGS. 7A and 7B, the distal end of the actuating rod 6 is received within and is attached to the tubular connector 156. When the biopsy jaws are in an open configuration as shown in FIG. 7A, the tubular portion 156 is contained within the body 136. When the jaws are actuated to a closed configuration as shown in FIG. 7B, by distally advancement of the control wire 6, the tubular portion 156 projects distally out of the opening 138 in the body. As the parts move from the configuration 7A to that shown in 7B, the actuator struts 148 cause the biopsy jaws to swing closed about the hinge lines 146A, 146B to sever tissue and capture the severed tissue between the jaws.

It may be noted that the cutting edges of the biopsy jaws 142A, 142B may be sufficiently sharp from the stamping operation itself, thereby avoiding the need to sharpen them in further manufacturing operations.

It also should be noted that although the embodiment illustrated in FIG. 7 is shown with living hinges at the hinge points, it may be desirable in some instances to substitute a more conventional, pin hinge for one or more of the hinge points.

FIGS. 8A-8F illustrate another embodiment of the invention in which the jaws are closed by pulling the control wire 60 in a proximal direction and are opened by pushing the control wire 60 in a distal direction. In this embodiment, a major portion of the biopsy jaws and their supporting elements may be formed from two identical elements stamped from sheet material such as suitable spring metal using conventional stamping techniques. As in the embodiment illustrated in FIG. 7, the identical halves are joined to form a biopsy jaw assembly which is mountable to the distal end of the elongate flexible plastic tubular shaft 4. As shown in FIGS. 8A and 8B, this embodiment of the invention includes a pair of identical halves 160A, 160B. Each of the halves is formed to include a proximal tube section 162A, 162B which, when the halves 160A, 160B are mated, will define a proximal tube 162 that is insertable into the distal end of the tube 4. The proximal tube portions 162A, 162B also may be provided with barbs as in the previously described embodiment (not shown). The proximal tube sections 162A, 162B each merge into an enlarged, bulbous body portion 164A, 164B which, when the halves are joined, will define a bulbous hollow body 164. A tubular segment 166A, 166B is formed in the upper portion of each body segment 164A, 164B to receive a portion of the actuating mechanism, as will be described. Extending from the distal portion of each of the body segments 164A, 164B is a retaining strap 168A, 168B. Biopsy jaws 170A, 170B are hingedly attached to the distal ends of the retaining straps 168A, 168B at a hinge line 172A, 172B. Preferably, the hinge line 172A, 172B may be stamped directly in its associated stamped half 160A, 160B between the proximal and distal ends of the jaws 170A, 170B. The lower end of each of the retaining straps 168A, 168B also defines a hinge line 174A, 174B at its juncture with its associated body portion 164A, 164B.

As in the previously described embodiment, in the embodiment of FIGS. 8A-8F the jaws are actuated between open and closed positions by operation of the control wire 6. In this embodiment, the jaws are opened by pushing on the control wire 6 and are closed by pulling on the wire 6. The distal end of the wire 6 is connected to the proximal ends of the biopsy jaws 170A, 170B in a manner as to define a hinge between the proximal ends of the jaws 170A, 170B and the distal end of the control wire 6. As illustrated in FIGS. 8C-8F, the control wire 6 may be connected to the proximal ends of the jaws 170A, 170B by an arrangement including a pair of connector tabs 180A, 180B formed integrally with the proximal end of the jaws 170A, 170B. The connector tabs 180A of one of the jaws 170A faces the connector tabs 180B of the opposing jaw half. A connector bar 182 (FIGS. 8C, 8D), having a pair of transversely extending wings 184 is sandwiched between the facing connector tabs 180A, 180B and the arrangement may be secured together as by spot welding, indicated at 186. The connector bar 182 is formed with a longitudinally extending channel 188 that receives and may be spot welded to the distal end of the control wire 6. The connector bar 182 also may carry a distally extending retention spike 190 to impale and help retain the biopsied tissue. FIG. 8F illustrates the manner in which the biopsy jaws may be open, by pushing on the control wire 6. The distal movement of the control wire 6 pushes the joint proximal ends of the biopsy jaws in a distal direction while the retaining straps 168A, 168B prevent the jaws from moving bodily distally with the control wire. Consequently, the jaws are cause to open, with the connector tabs 180A, 180B flexing, to define a living hinge, and also with the retaining straps 168 flexing apart. The jaws may be closed by pulling proximally on the control wire 6.

FIGS. 9A-9E illustrate still another embodiment of the invention, also in which the jaws are opened by pushing and closed by pulling on the control wire 6. This embodiment, as the others, is formed from a pair of identical halves that can be joined to each other in facing relation to form a proximal section that is mountable on the distal end of the tubular catheter and a distal section including the biopsy jaws mounted to be openable and closable upon actuation of the control wire. In this embodiment, the halves of the device each include a proximal tubular section 192A, 192B. A constricted region 194 may be formed in each of the tube sections 192A, 192B. Extending distally from the proximal tube 192 are a pair of retaining straps 196A, 196B which correspond substantially to the retaining straps 168A, 168B described in connection with the embodiment of FIG. 8. As with that embodiment, the retaining straps 196A, 196B are connected integrally to the biopsy jaws 198A, 198B distally of the proximal ends of those jaws. In this embodiment, a somewhat conventional pin type hinge 200 is formed at the proximal ends of the jaws 198A, 198B and serves to hingedly connect the proximal ends of the jaws 198A, 198B to the distal end of the control wire 6. The hinge elements 202A, 202B may be formed from tabs formed integrally with the biopsy jaws during the stamping operation. The hinge elements 202A, 202B are connected by a hinge pin 204 which completes the hinge 200. The hinge 200 is connected to the control wire 6 in the manner illustrated in FIG. 9C. As shown, the control wire 6 is connected to a wire extension 206 which, in turn, carries a transversely extending cylinder 208 that serves as part of the hinge assembly. The hinge element 208 is captured between the transversely spaced pairs of hinge elements 202A, 202B and receives the hinge pin 204. A retention spike 206 may be secured to and may extend distally from the hinge element 208.

Figure 10A:
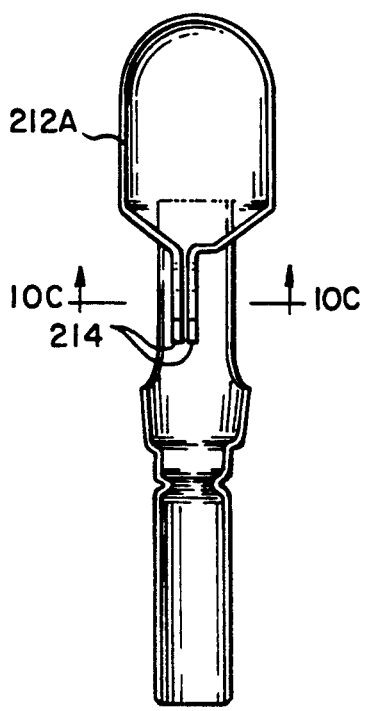
Figure 10C:
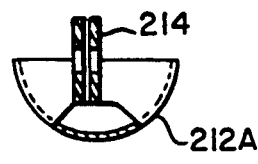
Figure 10D:
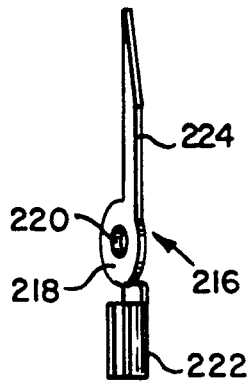
Figure 10B:
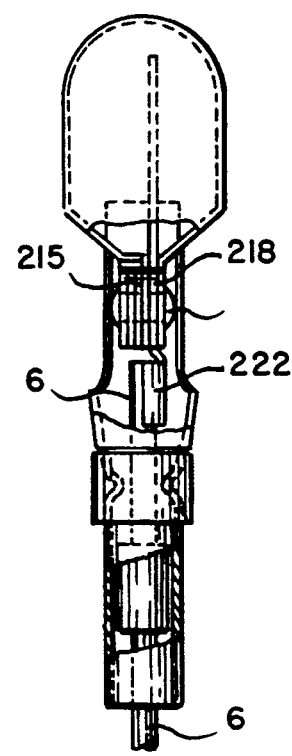
Figure 10E:
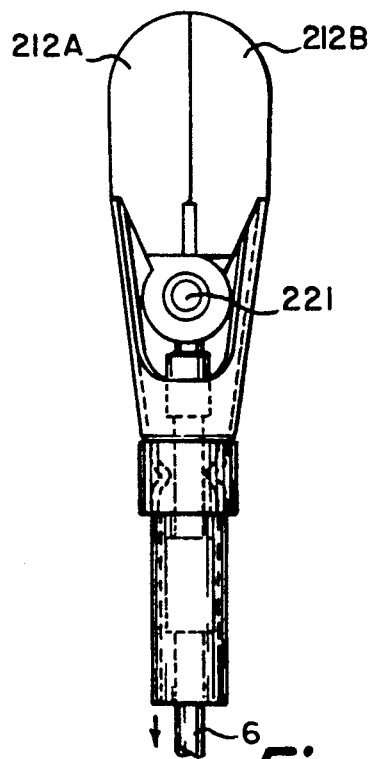
Figure 10F:
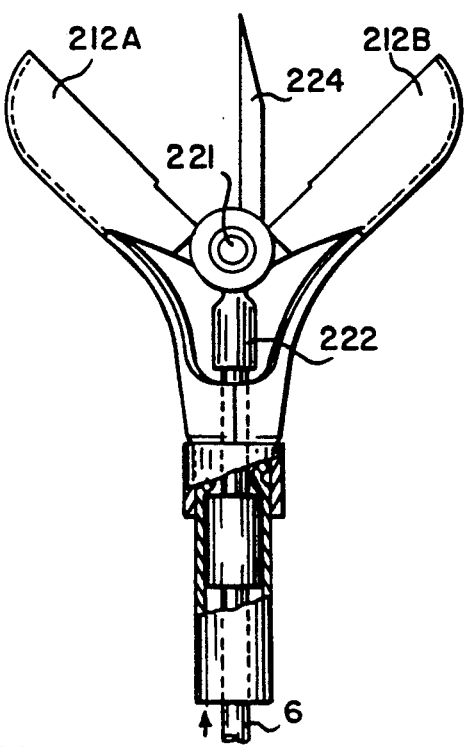

FIGS. 10A-10F illustrate still another embodiment of the invention which is similar to the embodiment disclosed in FIG. 9 except that it incorporates a modified form of hinge arrangement and connection of the hinge arrangement to the distal end of the actuating wire. As shown, in this embodiment each of the biopsy jaws 212A, 212B is formed to include a pair of hinge elements 214 which, when the device is assembled may be hinged together by a hinge pin. The hinge elements 214 can be stamped, formed and oriented using conventional stamping techniques as will be appreciated by those skilled in the art. Suitable washers 215 may be interposed as needed as suggested in FIG. 10B. The control wire 6 may be connected to the hinge by a connector element 216 (FIG. 10D) that has a flat central portion 218 with a central hole 220 to receive a hinge pin 221. The proximal end of the element 216 is formed to define a channel tube 22 that receives and may be welded to the distal end of the control wire 6 (FIG. 10B). Extending distally from the element 216 may be a retention spike 224. The operation of the embodiment as shown in FIGS. 10A-10F is essentially the same as that described in connection with the embodiment shown in FIGS. 8 and 9.

From the foregoing it will be appreciated that the invention provides biopsy catheters in which critical elements such as the jaws and cutting cups may be formed at a low cost by injection molding them from plastic, forming them from metal or plastic in an integral piece with their actuating devices. The actuating mechanisms for the cutting jaws are of relatively simple construction. Although the devices are suitable for use as a disposable item, to be used only once, they may be sterilized and reused, depending on the condition of the cutting edges. Where the device has a smooth outer surface, free of the numerous crevices inherent in prior spring covered devices, there is less chance for entrapment of debris and contaminants. It should be understood, however, that the foregoing description of the invention is intended merely to be illustrative thereof and that other modifications and embodiments may be apparent to those skilled in the art without departing from its spirit.

Having thus described the invention, what we desire to claim and secure by Letters Patent is:

1. A biopsy device comprising:
    an elongate flexible tubular shaft having a proximal end and a distal end;
    a biopsy jaw assembly mounted to the distal end of the shaft, the biopsy jaw assembly including supporting strut means mounted in a fixed position with respect to the distal end of the shaft, a pair of biopsy jaws hinged to the end of the support strut means for opening and closing movement toward and away from each other, an actuator strut hingedly connected to each of the biopsy jaws, each biopsy jaw and its associated support strut and actuator strut being formed in a one piece unitary structure; and
    a control wire extending longitudinally through the shaft and being connected to the proximal end of the actuating struts whereby longitudinal movement of the control wire may cause the biopsy jaws to open and close.

2. A biopsy device as defined in claim 1 wherein each biopsy jaw and its associated supporting and actuating struts are formed from a single unitary sheet of material.

3. A biopsy device as defined in claim 2 wherein the material comprises spring steel.

4. A biopsy device as defined in any one of claims 1-3 further comprising a connector at the proximal ends of the actuator struts for connection to the distal end of the control wire.

5. A biopsy device as defined in claim 4 wherein the support struts are mounted to the tubular member by a hollow body formed integrally in one piece with the support struts.

6. A biopsy device as defined in claim 5 wherein the connector between the control wire and the actuator struts is retractable into the hollow body when the jaws are in an open position.

7. A biopsy device as defined in claim 6 wherein the distal end of each actuator strut is connected at a living hinge to the biopsy jaw and at its proximal end to the connector for the control wire.

8. A biopsy device as defined in claim 5 wherein the distal end of each actuator strut is connected at a living hinge to the biopsy jaw and at its proximal end to the connector for the control wire.

9. A biopsy device as defined in claim 4 wherein the distal end of each actuator strut is connected at a living hinge to the biopsy jaw and at its proximal end to the connector for the control wire.

10. A biopsy device as defined in any one of claims 1-3 further comprising a connector at the proximal ends of the actuator struts for connection to the distal end of the control wire and wherein the distal end of each actuator strut is connected at a living hinge to the biopsy jaw and at its proximal end to the connector for the control wire.

11. A biopsy device as defined in claim 1 further comprising:
    the supporting strut means having a distal end attached to the biopsy jaws at a location substantially distally of the proximal ends of the biopsy jaws;
    said actuator strut means connecting the distal end of the control wire and the proximal end of the biopsy jaws;
    the connection between the control wire and biopsy jaws enabling relative pivotably movement of the jaws about that connection;
    the supporting strut means being constructed to permit the biopsy jaws to separate and open.

12. A biopsy device as defined in claim 11 wherein the connection between the control wire and the proximal ends of the biopsy jaws comprises a flexible, living hinge.

13. A biopsy device comprising:
an elongate flexible tubular shaft having a proximal end and a distal end;
a biopsy jaw assembly mounted to the distal end of the shaft, the biopsy jaw assembly being formed from a pair of substantially identical subassemblies joined to each other in facing relation, each of said subassemblies including a biopsy jaw, a means for mounting the biopsy jaw assembly on the distal end of the shaft and actuating means connected to each biopsy jaw and being operable from the proximal end of the biopsy device to open and close the biopsy jaws, each biopsy jaw and its associated mounting means and actuating means being a one-piece unitary structure;
each of the biopsy jaw subassemblies being stamped from a sheet of spring steel.

14. A biopsy device comprising:
an elongate flexible tubular shaft having a proximal end and a distal end;
a biopsy jaw assembly mounted to the distal end of the shaft, the biopsy jaw assembly including supporting means mounted in a fixed position with respect to the distal end of the shaft, a pair of biopsy jaws hinged to the ends of the support means and about which the jaws may pivot between open and closed position, an actuator hingedly connected to each of the biopsy jaws; and a control wire extending longitudinally through the shaft and being connected to the proximal end of the actuator means whereby longitudinal movement of a control wire may cause the biopsy jaws to open and close;
the support means comprising supporting strut means and the actuator means comprising an actuator strut hingedly connected to each of the biopsy jaws, each biopsy jaw and its associated support strut and actuator strut being formed in a one-piece unitary structure.

15. A biopsy device as defined in claim 14 wherein the support means comprises a retaining strap, the biopsy jaws being hinged to the distal end of the retaining straps at a hinge point between the proximal and distal extremities of the jaws at a location substantially distally of the proximal end of the biopsy jaws and where the actuator member is pivotably attached to the proximal ends of the biopsy jaws.

* * * * *